(12) United States Patent
Maeda et al.

(10) Patent No.: US 10,781,440 B2
(45) Date of Patent: Sep. 22, 2020

(54) OPERATION METHOD FOR CONTROL MATERIALS AND AUTOMATED ANALYZER

(71) Applicant: Hitachi High-Tech Corporation, Minato-ku, Tokyo (JP)

(72) Inventors: Kohshi Maeda, Tokyo (JP); Terumi Tamura, Tokyo (JP); Daisuke Morishima, Tokyo (JP)

(73) Assignee: Hitachi High-Tech Corporation, Tokyo (JP)

( * ) Notice: Subject to any disclaimer, the term of this patent is extended or adjusted under 35 U.S.C. 154(b) by 164 days.

(21) Appl. No.: 15/550,502

(22) PCT Filed: Feb. 23, 2015

(86) PCT No.: PCT/JP2015/054906
§ 371 (c)(1),
(2) Date: Aug. 11, 2017

(87) PCT Pub. No.: WO2016/135799
PCT Pub. Date: Sep. 1, 2016

(65) Prior Publication Data
US 2018/0030433 A1 Feb. 1, 2018

(51) Int. Cl.
*C12N 15/10* (2006.01)
*C12Q 1/68* (2018.01)
(Continued)

(52) U.S. Cl.
CPC ....... *C12N 15/1013* (2013.01); *C12Q 1/6806* (2013.01); *G01N 35/0092* (2013.01);
(Continued)

(58) Field of Classification Search
None
See application file for complete search history.

(56) References Cited

U.S. PATENT DOCUMENTS 6,984,527 B2 * 1/2006 Miller ................... G01N 35/00
422/562
2005/0037502 A1 2/2005 Miller
(Continued)

FOREIGN PATENT DOCUMENTS

JP 2007-502412 A 2/2007
JP 2007-212303 A 8/2007
(Continued)

OTHER PUBLICATIONS

International Search Report (PCT/ISA/210) issued in PCT Application No. PCT/JP2015/054906 dated Jun. 2, 2015 with English translation (Four (4) pages).

*Primary Examiner* — Kathryn Wright
(74) *Attorney, Agent, or Firm* — Crowell & Moring LLP

(57) ABSTRACT

An automatic analyzer including a function for operating control materials and its operation method are provided. The analyzer is configured to start sampling by giving priority to an entirety of control materials corresponding to all assay items required for measurement. The analyzer is also configured to automatically start sampling of a patient specimen based on a preliminarily set sampling timing after completion of sampling of the entirety of control materials. The analyzer is also configured to stop, when an abnormality is present in a measurement result of at least any one of control materials in the group of control materials, sampling of a patient specimen corresponding to a control material in which the abnormality is found, and notify a tester of the abnormality.

6 Claims, 7 Drawing Sheets

(51) Int. Cl.
   *G01N 35/00* (2006.01)
   *C12Q 1/6806* (2018.01)
   *C12M 1/36* (2006.01)
(52) U.S. Cl.
   CPC ........... *G01N 35/0095* (2013.01); *C12M 1/36* (2013.01); *C12Q 2565/00* (2013.01)

(56) References Cited

U.S. PATENT DOCUMENTS

| | | |
|---|---|---|
| 2007/0183926 A1 | 8/2007 | Tanoshima |
| 2012/0029934 A1 | 2/2012 | Shindo et al. |
| 2014/0193893 A1 | 7/2014 | Ishizawa et al. |
| 2014/0295453 A1 | 10/2014 | Hirata et al. |

FOREIGN PATENT DOCUMENTS

| | | |
|---|---|---|
| JP | 2010-133870 A | 6/2010 |
| JP | 2011-220857 A | 11/2011 |
| JP | 2012-26947 A | 2/2012 |
| JP | 2013-32921 A | 2/2013 |
| JP | 2013-185975 A | 9/2013 |
| JP | 2014-194400 A | 10/2014 |

* cited by examiner

FIG. 6D

PERFORM SETTING FOR SAMPLING AUTOMATIC STOPPING.
SELECT CONDITIONS FOR SAMPLING AUTOMATIC STOPPING.

611
○ DO NOT AUTOMATICALLY STOP SAMPLING.
◉ AUTOMATICALLY STOP SAMPLING WHEN PREDETERMINED AMPLIFICATION DETERMINATION IS CONTINUOUSLY RECOGNIZED. ← 612
NUMBER OF PREDETERMINED CONTINUOUS AMPLIFICATION DETERMINATIONS:

613

| ASSAY ITEM | STOP SETTING | NUMBER OF CONTINUOUS DETERMINATIONS |
|---|---|---|
| ITEM A | ☑ | 20 |
| ITEM B | ☑ | 15 |
| ITEM C | ☐ | NA |
| ITEM D | ☑ | 10 |
| ITEM E | ☑ | 30 |
| ITEM F | ☑ | 5 |
| ITEM G | ☐ | NA |
| ITEM H | ☐ | NA |
| ITEM I | ☐ | NA |
| ITEM J | ☑ | 15 |
| ITEM K | ☑ | 15 |
| ITEM L | ☐ | NA |
| ITEM M | ☐ | NA |
| ITEM N | ☑ | 10 |

PERFORM TRANSMISSION SETTING FOR MEASUREMENT RESULT DETERMINATION INFORMATION INCLUDING CONTROL MATERIAL.
SELECT CONDITIONS FOR TRANSMISSION OF MEASUREMENT RESULTS.

◉ AUTOMATICALLY REPORT ONLY DETERMINED RESULTS. ~~614
○ AUTOMATICALLY REPORT RESULTS INCLUDING PENDING RESULTS.

615

[ OK ]

OPERATION METHOD FOR CONTROL MATERIALS AND AUTOMATED ANALYZER

TECHNICAL FIELD

The present invention relates to a method and program for operating a control material, and a device including a function for operating the control material.

BACKGROUND ART

The following contents are described in 42 CFR 493.1256 Standard: Control procedures. The control procedures must detect immediate errors that occur due to test system failure, adverse environmental conditions, and operator performance. For each test system, the test laboratory must perform control procedures using the number and frequency specified by the manufacturer. At least once each day patient specimens assayed or examined perform the following:

a) each quantitative procedure, including two control materials of different concentrations; and b) each qualitative procedure, including a negative and positive control material.

According to the Chinese standards (YY), in order to detect an abnormality in an analytic process, a reagent for simultaneously measuring an internal control material (hereinafter referred to as "IC") in the same process as that for a target nucleic acid is required.

The high-concentration and low-concentration control material is intended to confirm whether or not the quantitative performance of a test system or a test reagent satisfies a target performance. The positive control material is intended to confirm whether or not an abnormality is present in a reagent, a test system, or test circumstances. In the case of a laboratory shared by manual test, a false positive may occur in the negative control material due to contamination of the laboratory, and thus the negative control material is intended to confirm whether or not this abnormality is present. The internal control material is a control material to be amplified together with a target nucleic acid in a reaction liquid, and is intended to confirm whether or not an abnormality is present in a treatment process for each test. Although minimum operation for control material standards are provided as described above, an actual operation method for control materials, for example, at which timing a measurement for control materials is made in an analytic process for one day, varies depending on test laboratories. In the related art, the above-mentioned group of control materials is operated by an operator to ensure the test quality according to the individual rules for each test laboratory, and the operator confirms that the test quality is ensured based on the measurement results for control materials and reports the test results to a higher level.

SUMMARY OF INVENTION

Technical Problem

Since the actual operation method for control materials, for example, at which timing a measurement for control materials is made in an analytic process for one day, varies depending on test laboratories, there is a disadvantage that the actual operation method for control materials is not suitable for the operation method for the laboratory when control materials are fully automatically operated. Further, it has been necessary for a user to determine whether or not a measurement for control materials is required, a measurement timing, and operations such as stopping of a device depending on a measurement result. Accordingly, each tester needs to be highly trained. Further, when an abnormality in a control material is caused due to a common reagent, such as an extraction reagent, or a common mechanism such as a system, an abnormality determination is made in the subsequent measurement processes. Accordingly, in the case of a fully automatic test, reagents and consumables are wasted. As a timing for measurement for control materials in an analytic process for one day, assuming that all measurements of control material for assay items to be measured are made, for example, when all control materials in the assay item for which the measurement is scheduled are measured at the beginning of a day, if the measurement for the day is stopped before completion of measurement of patient specimens corresponding to the control materials, control materials, reagents, and consumables for the measured control materials are wasted. Further, if a positive test result is continuously made due to contamination of a part of the measurement circumstances during a fully automatic test, specimens, reagents, and consumables are wasted.

Solution to Problem

In order to solve the above-mentioned problems, the present inventors have researched and earnestly studied operation method for control materials and the like of a plurality of test laboratories, and have solved the above-mentioned problems by implementing a configuration and function necessary for a fully automatic operation for control material.

That is, an automatic analyzer includes: a dispensing unit; a holding unit that holds a group of control materials accessible as needed by the dispensing unit; a processing unit that performs an assay preparation process on a patient specimen/control material; an analytical unit that performs an assay of the patient specimen/control material undergone the assay preparation process; a data analysis unit that analyzes a result of the assay; a database that holds a plurality of operation processes for control material; an input unit that selects the operation processes; and a control unit that controls the dispensing unit, the holding unit, the processing unit, the analytical unit, the data analysis unit, the database, and the input unit. A control material/patient specimen and/or measurement result information is operated according to a preliminarily set operation process.

Further, in the device, some of the items to be confirmed in each control material are replaced with ones from the measurement result of a patient specimen including an internal control material (hereinafter referred to as "IC"). Specifically, when the measurement result of the patient specimen is positive, determination and reporting are sustained in consideration of the possibility of a false positive due to contamination of a laboratory. After that, when the measurement result of the patient specimen is negative, the quality of the analytic process by the IC is ensured, and thus the determination is promptly made. Further, since the measurement result is negative and thus the possibility of occurrence of a false positive due to contamination of the circumstance of the laboratory is denied, the positive test results for which the determination has been suspended are promptly determined. The determined measurement results include a setting capable of performing an automatic reporting promptly to a higher level. With this configuration, the test quality is ensured, the number of measurements for control materials is minimized, and the measurement results can be reported promptly to a higher level. Further, the device has a function in which the preliminarily set operation processes for control material/patient specimen include the following three processes: 1) a first process is to start the assay preparation process by giving priority to all groups of control materials corresponding to all assay items required for measurement; 2) a second process is to automatically start the assay preparation process and sampling of a patient specimen after completion of sampling of all the groups of control materials; and 3) a third process is to stop sampling of a patient specimen corresponding to a control material in which an abnormality is found, when an abnormality is present in a measurement result of a group of control materials, and to notify a tester of the abnormality. The device further has a function capable of setting and/or processing for temporarily stopping sampling of a patient specimen corresponding to a group of control materials before completion of measurement of another assay item when an abnormality is present in a measurement result of a group of control materials in a certain assay item. Further, the device has a function for automatically resuming the sampling when no abnormality is present in the measurement result for control materials for the patient specimen temporarily stopped before completion of the measurement for control materials.

Further, the device has a function in which the operation processes for control material that can be preliminarily set include: 1) starting the assay preparation process by giving priority to all groups of control materials corresponding to an assay item having an N-th highest priority and required for measurement, and automatically starting the assay preparation process for patient specimens corresponding to the groups of control materials after completion of sampling of all the groups of control materials; 2) automatically starting the assay preparation process by giving priority to all groups of control materials corresponding to an assay item having an (N+1)-th highest priority after completion of patient specimen sampling corresponding to 1), and automatically starting the assay preparation process for patient specimens corresponding to the groups of control materials after completion of sampling of all the groups of control materials; and 3) stopping, when an abnormality is present in a measurement result of a group of control materials, sampling of a patient specimen corresponding to a control material in which the abnormality is found, and notifying a tester of the abnormality.

Further, the device has a function in which when a positive test result is obtained for a measurement result of a patient specimen measured in an N-th order, transmission of measurement result information to a higher level is suspended, and when a measurement result of a patient specimen measured in an (N+1)-th order or later shows a negative determination and a result of internal control material shows a normal determination, the measurement results and the suspended measurement result information obtained in the N-th measurement are transmitted to the higher level. Further, the device has a function in which the input unit for selecting an operation process includes a setting item for selecting whether or not a measurement for control materials is required after completion of measurement; and a control material that is automatically set after completion of a requested measurement is measured for a setting for instructing a measurement for control materials in the setting item.

Further, the device has a function in which: the input unit for selecting an operation process includes a setting item for setting an automatic measurement of a negative control material when a predetermined number of positive test results are continuously detected; and a negative control material is automatically analyzed when a predetermined number of continuous positive test results are obtained for the setting for instructing the measurement for control materials in the setting item, and when the negative control material is determined to be abnormal, the user is notified of the abnormality. The input unit for selecting an operation process includes an input unit capable of inputting a numerical value as the number of continuous positive test results for each test item, and an automatic operation is performed according to the setting. Further, the device has a function in which, during an automatic analysis of a negative control material, sampling of a patient specimen is temporarily stopped, and when a result of the assay of the negative control material is normal, the sampling is resumed.

Further, the device has a function in which: the input unit for selecting an operation process includes a setting item for setting an automatic measurement of a predetermined group of control materials when a predetermined number of IC abnormality determinations are continuously detected; when the setting item is set and operated, a group of control materials is automatically analyzed when a predetermined number of continuous IC abnormality determination results are obtained; and when the group of control materials is determined to be abnormal, the user is notified of the abnormality. Further, the input unit for selecting an operation process includes an input unit capable of inputting a numerical value as the number of continuous abnormality determinations for each test item, and an automatic operation is performed according to the setting. Further, the device has a function for temporarily stopping sampling of a patient specimen during the automatic analysis of a group of control materials, and resuming the sampling when the analysis result of the group of control materials is normal.

Advantageous Effects of Invention

An optimum operation for each test laboratory can be performed by implementing the above-mentioned means and by fully automatically operating the device according to operation processes preliminarily set. Further, since the system can automatically perform the operations, such as determination as to whether or not a measurement is required, a measurement timing, and stopping of the device, the system can be operated by anyone other than a highly trained tester. Further, when there is a possibility that an abnormality result control material is caused due to the entire laboratory, a common reagent, or a common mechanism, the subsequent sampling processes are promptly stopped so as to prevent wasting of reagents and consumables. Further, the test of a patient specimen that can be tested in the absence of a tester can be conducted by automatically resuming sampling of a patient specimen in the assay item including measurement results for control materials indicating that there is no problem. Further, a measurement for control materials can be executed immediately before a timing at which a measurement for control materials is necessary, and even when the scheduled test is canceled during the test, control materials, reagents, and consumables can be prevented from being wasted. Also in a test laboratory or an area in which a measurement is scheduled before and after the measurement of a patient specimen as an operation method for control materials, the measurement result can be sequentially reported to a higher level based on the measurement result of each patient specimen, even if the measurement for control materials is not made for the same assay item a plurality of times. The number of measurements for control materials can be reduced by performing the measurement for control materials only when the measurement results of one or more measurements show a positive test result after completion of the measurement. When positive test results in which a risk of contamination is taken into consideration are continuously detected, it can be automatically confirmed whether or not the analytic process is excellent. Further, an optimum operation can be performed for each test laboratory and for each assay item by setting a numerical value as an optimum number of continuous positive test results for each test item or for each test laboratory. Furthermore, when it is assumed that there is a high risk of contamination in the measurement circumstances, sampling is automatically temporarily interrupted so as to prevent wasting of specimens, reagents, and consumables when the contamination is actually present.

BRIEF DESCRIPTION OF DRAWINGS

FIG. 4 is a diagram for explaining an analytical unit.

FIG. 6D is a diagram illustrating a specific example of the screen setting for control material.

FIG. 6E is a diagram illustrating a specific example of the screen setting for control material.

DESCRIPTION OF EMBODIMENTS

Best modes for embodiments of the invention for dynamically operating a control material will be described in detail below with reference to the drawings.

The present invention relates to a fully automated analyzer that performs automatic measurement of groups of control materials respectively corresponding to a plurality of assay items and patient specimens and reports measurement results. As a specific example of this embodiment, a fully automatic genetic testing device that performs an automatic analysis of analysis methods using a nucleic acid extraction method using magnetic beads and a real-time PCR method. Note that as the nucleic acid extraction method, for example, an extraction method using a column may be employed. As the analysis method, for example, an isothermal amplification method, such as a LAMP method, a NASBA method, or a TRC method, may be employed. Thus, this embodiment can be carried out in various methods, and a difference between the extraction method and the test method does not limit the invention herein proposed.

Figure 1:
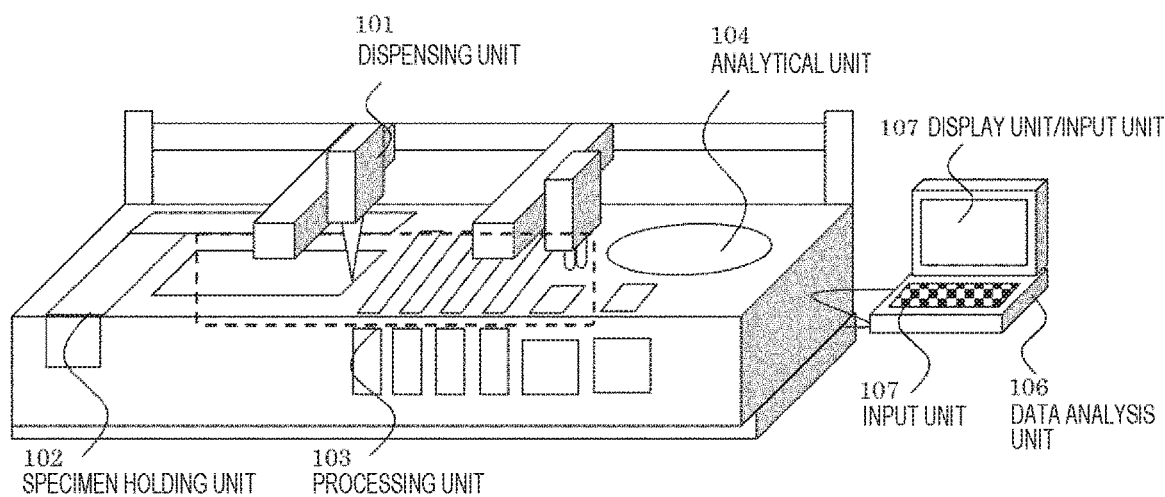
FIG. 1 is a diagram for explaining an automated analyzer.

As illustrated in FIG. 1, a minimum configuration for implementing this embodiment is a device configuration including: a dispensing unit 101; a specimen holding unit 102 that holds a patient specimen and a group of control materials that are accessible, as needed, by the dispensing unit; a processing unit 103 that performs an assay preparation process on a patient specimen/control material; an analytical unit 104 that performs an assay of the patient specimen/control material on which the analysis preparation has been performed; a data analysis unit 106 that analyses a result of the assay; a database that holds a plurality of operation processes for control material; a display unit/input unit 107 that selects the operation processes; and a control unit that controls these units. More specifically, the input unit includes a setting item indicating that sampling of a patient specimen corresponding to a group of control materials before completion of measurement of another assay item is temporarily stopped when an abnormality is present in a measurement result of a group of control materials in a certain assay item.

A patient specimen in this embodiment refers to an unknown specimen. Specifically, it is unknown whether an object in the assay item of this embodiment is contained in the specimen or not, and the concentration of the object is also unknown. Specific examples of the specimen include a serum specimen and a plasma specimen which are derived from a patient.

As for a control material in this embodiment, a positive control material and a negative control material are used for a qualitative test, and a high-value control material, a low-value control material, and a negative control material are used for a quantitative test. An internal control material is used for both the quantitative test and the qualitative test. The high-value control material and the low-value control material are intended to confirm whether a test system or a quantitative performance of a reagent satisfy a target performance. The positive control material is intended to confirm whether or not there is an abnormality in a reagent or a system. In the case of a laboratory shared by a manual test, a false positive may occur in the negative control material due to contamination of the laboratory. Therefore, the negative control material is intended to confirm whether or not such an abnormality is present. The internal control material refers to a control material that is amplified together with a target nucleic acid in a reaction liquid, and is intended to confirm whether or not an abnormality is present in each test treatment process. The group of control materials in this embodiment refers to a group of the plurality of control materials.

The dispensing unit 101 in this embodiment includes, as specific examples, a syringe mechanism including a nozzle for sucking a specimen and a tube through which the syringe mechanism is coupled to the nozzle, and an operation unit for allowing the nozzle to be movable in three axis directions of XYZ directions. More preferably, the XY operation unit may be a mechanism for rotational transfer in a θ direction. The dispensing unit 101 may have any configuration as long as the dispensing unit has a function for sucking a specimen and discharging the specimen to a target location, and is not limited to the above-mentioned specific example.

Figure 2A:
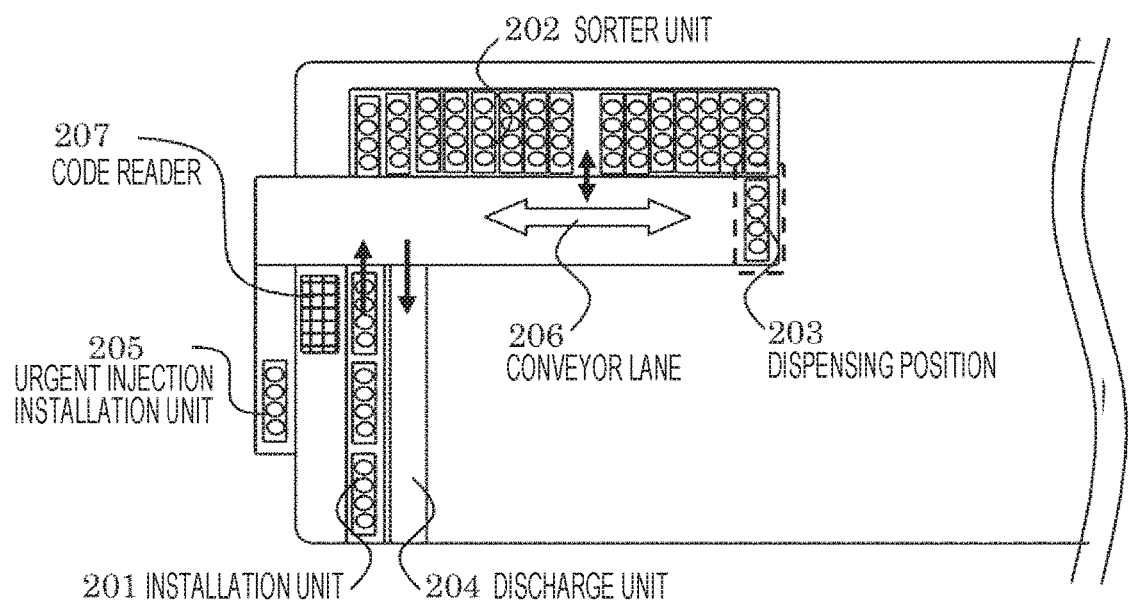
FIG. 2A is a diagram for explaining a control material holding unit.
Figure 2B:
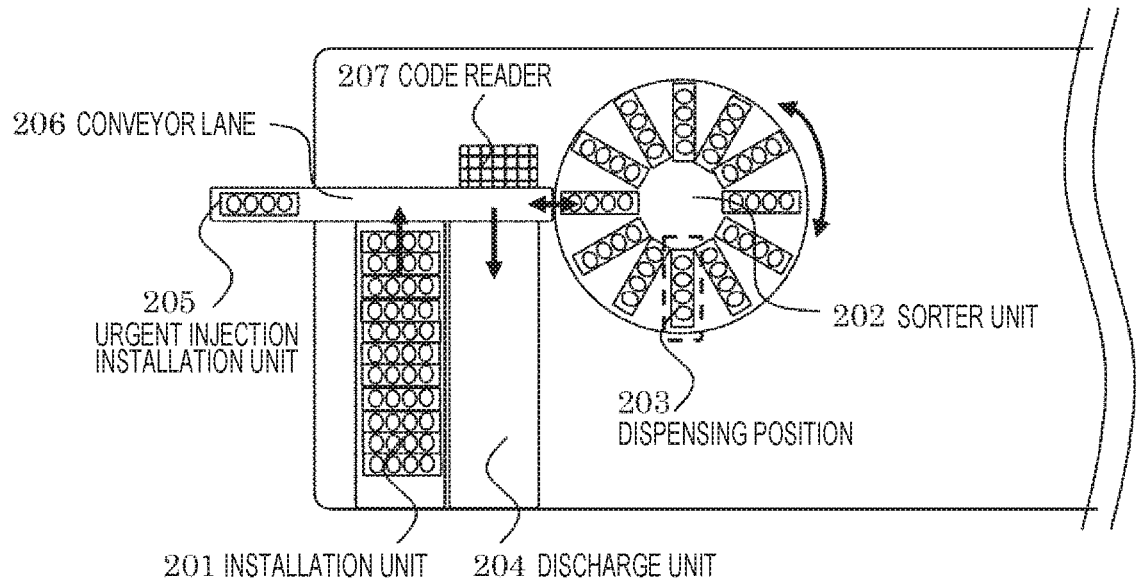
FIG. 2B is a diagram for explaining the control material holding unit.

The specimen holding unit 102 in this embodiment includes, as specific examples, at least an installation unit 201, a discharge unit 204, a sorter unit 202, and a conveyor lane 206, as illustrated in FIG. 2A, and has a dispensing position where the dispensing unit is accessible. More preferably, the specimen holding unit 102 includes an urgent injection installation unit 205 and a code reader 207. The installation unit 201 has a function for installing a group of control materials and a patient specimen which can be easily accessible by a tester. More preferably, the specimen holding unit 102 includes a code reader 207 that detects an ID of a control material or a patient specimen. The sorter unit 202 has a function in which the system holds a group of control materials and conveys a necessary control material to the dispensing position 203 according to a timing necessary for the system to perform a measurement. The configuration of another specific example of the holding unit is illustrated in FIG. 2B. In any configuration, the holding unit is not limited to the above-mentioned specific examples, as long as the holding unit can hold a patient specimen and a group of control materials in a system and can convey a predetermined patient specimen and control material to a dispensing position in response to a system process request.

Figure 3:
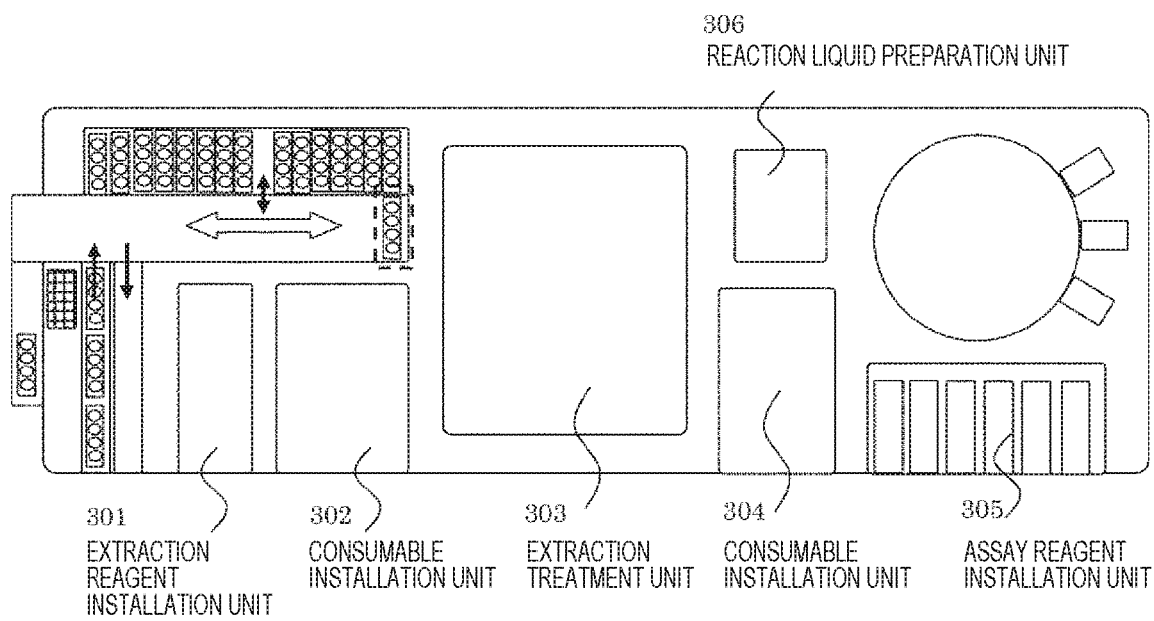
FIG. 3 is a diagram for explaining a processing unit.

The processing unit 103 in this embodiment includes, as specific examples, an extraction reagent installation unit 301, an extraction consumable installation unit 302, an extraction treatment unit 303, an analysis consumable installation unit 304, an assay reagent installation unit 305, and a reaction liquid adjustment unit 306, as illustrated in FIG. 3. The extraction reagent installation unit 301 is an area in which reagents necessary for nucleic acid extraction are installed. Each of the extraction consumable installation unit 302 and the analysis consumable installation unit 304 is an area in which consumables necessary for extraction processing and analysis processing are installed. The extraction treatment unit 303 is a unit that performs a treatment for extracting a nucleic acid from a specimen. The reaction liquid preparation unit 306 is a unit that prepares a reaction liquid by mixing a nucleic acid specimen extracted from a specimen by the extraction treatment unit 303 with an assay reagent.

As a specific processing operation of the processing unit, a specimen supplied from a specimen container is dispensed into an extraction container, and a solution for dissolving a protein component is added and dissolved for a predetermined time at a predetermined temperature. Magnetic beads for coupling a reagent for precipitating a nucleic acid with a nucleic acid are added to the solution to be agitated. The magnetic beads on which the nucleic acid in the extraction container is adsorbed are collected by a magnet to separate the nucleic acid from foreign components, and then the foreign components are discarded and a cleaning solution is added. The collected beads and the cleaning solution are suspended and the magnetic beads are collected by a magnet, and then the cleaning solution is discarded. A cleaning process is repeated a plurality of times. Lastly, the elute is suspended in the magnetic beads to elute the nucleic acid into an eluate, thereby obtaining a nucleic acid extraction liquid. In the reaction liquid preparation unit, the nucleic acid extraction liquid and the assay reagent are mixed in the reaction container and the reaction container is introduced into the analytical unit. The processing unit 303 in this embodiment is not limited to the specific example of the configuration, as long as the processing unit includes a mechanism necessary for executing a predetermined treatment.

The analytical unit 104 is a unit that performs an assay of the reaction process of the prepared reaction liquid. In the analytical unit 104, the fluorescence intensity is measured over time simultaneously with the application of a heat cycle amplified by PCR to the reaction liquid, and measurement data is sent to the data analysis unit. More preferably, as illustrated in FIG. 4, a reaction block 401 which can implement a PCR heat cycle is disposed on the circumference of a disk 402. Further, a detector 403 is disposed on the outside of the disk 402. While the reaction block 401 on which the reaction container is placed implements a predetermined PCR heat cycle (for example, pre-heating for 10 minutes at 95° C., and 50 cycles when 95° C.>55° C.>72° C.), the disk 402 is periodically rotated (for example, once every 10 minutes), so that the fluorescence intensity of the reaction liquid held in the reaction block 401 can be detected by the detector 403 over time. The analytical unit in this embodiment is not limited to the above-mentioned specific example, as long as the analytical unit can detect an analytical reaction.

The data analysis unit 106 in this embodiment includes a data storage unit 406 that accumulates data detected in the analytical unit 104; a database that holds parameter information necessary for assay; a data arithmetic unit 407 that calculates data using a predetermined analysis program based on the parameter information; and a display unit 107 that displays the analysis result. With this configuration, data detected in the analytical unit is stored in the data storage unit and analyzed based on the parameter information stored in the database, and the data arithmetic unit calculates a Ct value. When the assay item indicates a quantitative test item, the data arithmetic unit converts the Ct value into a concentration by referring to calibration data stored in the database. More specifically, detected data at a predetermined temperature in one cycle is selected from fluorescence detected data which is detected periodically (for example, once every 10 seconds). The detected data indicates relationships between the number of cycles and a fluorescence intensity. When the PCR amplification reaction advances, the fluorescence intensity indicated by the data increases as the number of cycles increases. In the case of a graph in which the vertical axis represents a fluorescence intensity and the horizontal axis represents the number of cycles, an S-shaped curve (amplification curve) is depicted. As parameter information for determining that the fluorescence intensity of the amplification curve has increased, a predetermined fluorescence intensity value is stored as Threshold Level. The data analysis unit 106 refers to the parameter of Threshold Level in the predetermined assay item from the database, and the data arithmetic unit calculates the point of intersection between the parameter and an amplification curve as the Ct value. When the assay item indicates a quantitative test item, the data arithmetic unit converts the Ct value into a concentration value by referring to the calibration data stored in the database in advance, and the display unit displays the concentration value. When the measured specimen is a positive control material (or a high-concentration control material or a low-concentration control material) or an internal control material, the data arithmetic unit determines whether the Ct value or the concentration value falls within a predetermined range by referring to a predetermined range of control material stored in the database, and when the Ct value or the concentration value falls outside of the predetermined range, the display unit displays warning. While this embodiment illustrates an analysis method using real-time PCR, the present invention is not limited to the above-mentioned specific example, as long as the data analysis unit in this embodiment can analyze the detected data and the display unit can display the analysis result and determination information indicating the analysis result.

The input unit in this embodiment includes an interface with which a user can input text and an input screen. Specific examples of the interface include a touch panel, a keyboard, and a mouse.

Figure 5A:
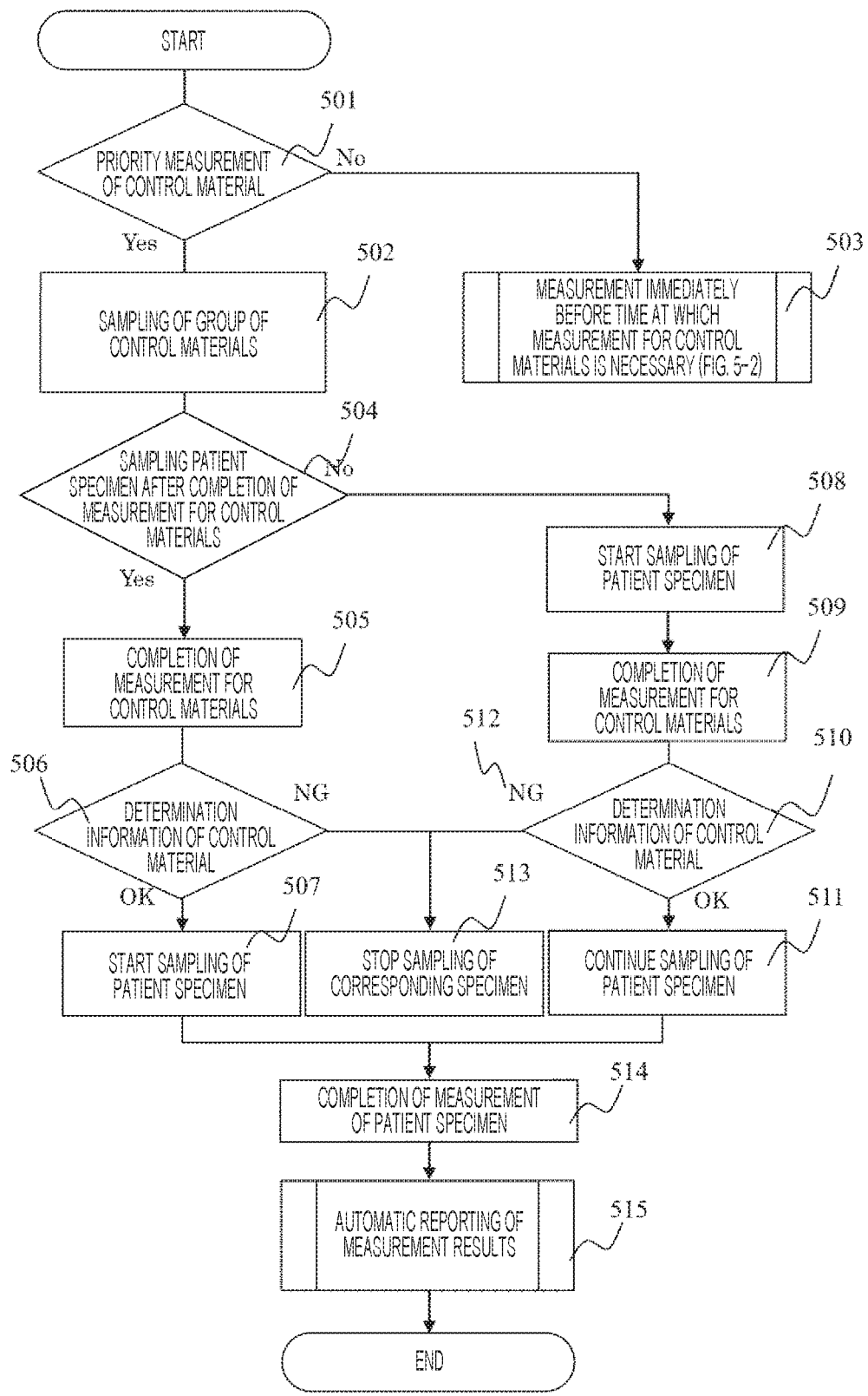
FIG. 5A illustrates a flowchart of an operation method for control materials.
Figure 5B:
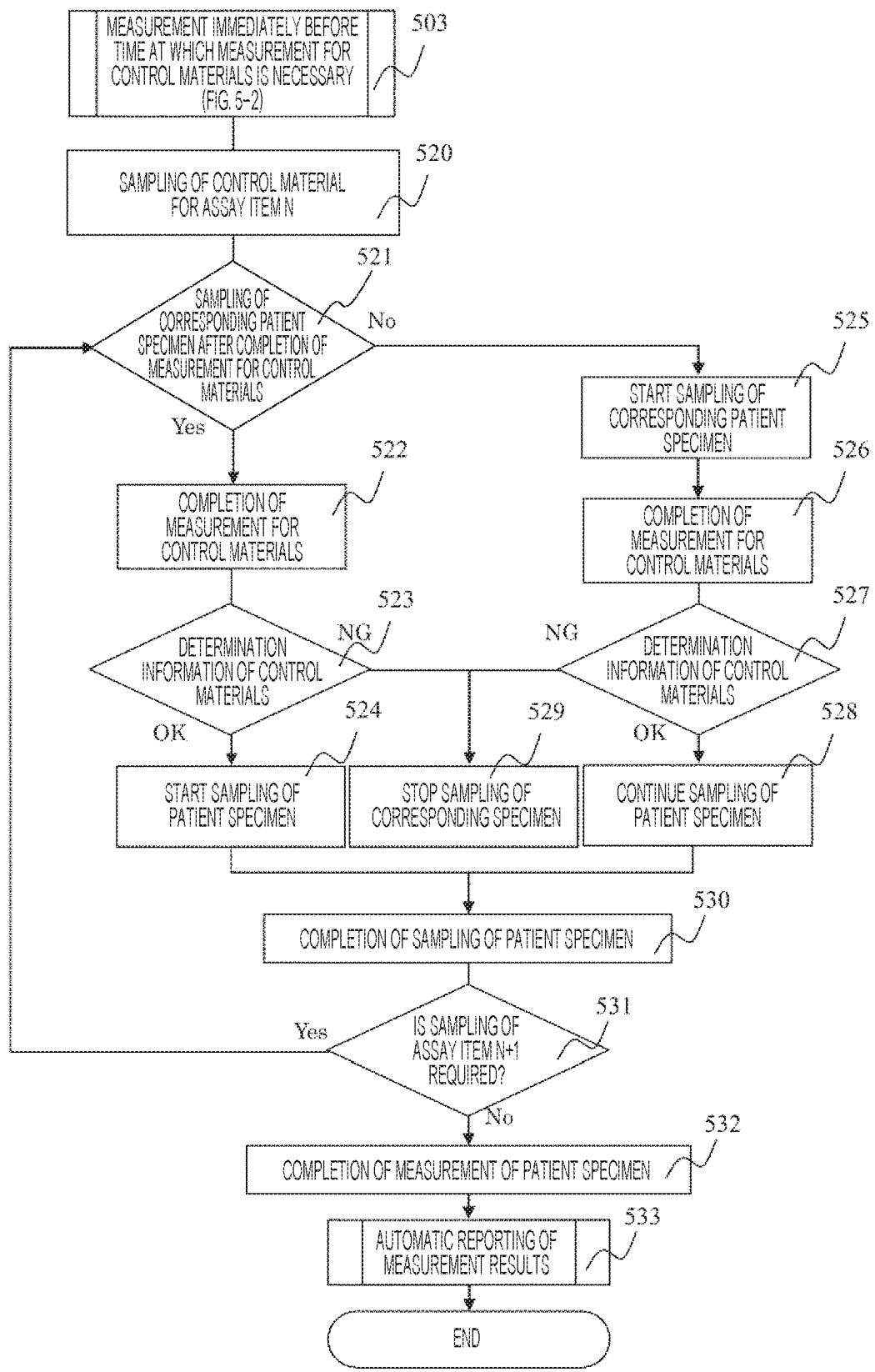
FIG. 5B illustrates a flowchart of the operation method for control materials.
Figure 6A:
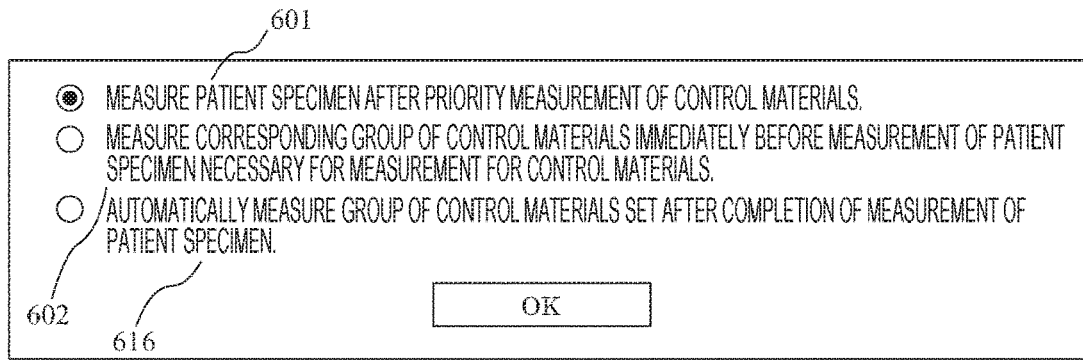
FIG. 6A is a diagram illustrating a specific example of a screen setting for control material.

As the embodiment using the device configuration described above, a specimen group in which an HCV patient specimen, an HBV patient specimen, and an HIV patient specimen are randomly arranged and a specific example of measurement of the groups of control materials respectively corresponding to these specimens will be described with reference to the flowcharts of the operation method for control materials illustrated in FIGS. 5A and 5B and screen settings for control material illustrated in FIGS. 6A, 6B 6C, 6D, and 6E. A device configuration in setting for priority measurement of control material will be described below. The input unit 107 of the device that implements this embodiment includes a setting screen as illustrated in FIG. 6A in association with the device operation process. The user inputs a setting 601 which indicates a priority measurement of control material. The user installs patient specimen groups and groups of control materials corresponding to the patient specimen groups in the specimen holding unit 102, and installs an assay reagent in the assay reagent installation unit 305. When a start button is pressed, the device that implements this embodiment starts "sampling of group of control materials" 502 in an order corresponding to the order of arrangement of patient specimens.

Figure 6B:
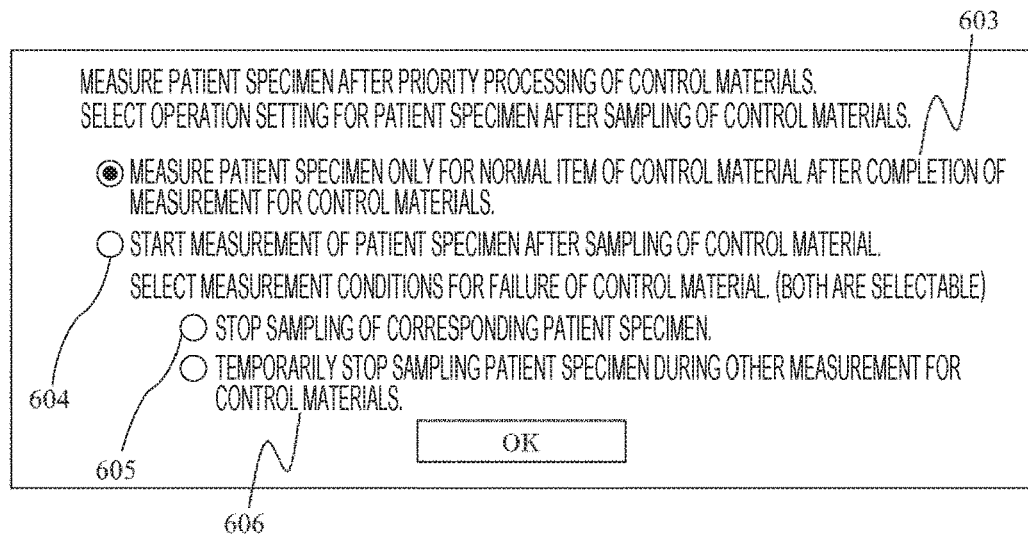
FIG. 6B is a diagram illustrating a specific example of the screen setting for control material.

Preferably, as illustrated in FIG. 6B, the setting screen includes an item for setting whether or not to wait for the measurement result for control materials as a sampling timing for each patient specimen. In the case of "setting for executing sampling of a patient specimen without waiting for the measurement result for control materials" 604, after completion of sampling of all groups of control materials, "sampling of a patient specimen" 508 is started without waiting for the measurement result of the group of control materials. In the case where the measurement time for the assay item is long, the throughput is extremely lowered after waiting for the completion of measurement of the group of control materials, and thus a maximum throughput can be ensured by starting sampling of patient specimens without waiting for the completion of the measurement. At this time, specifically, the patient specimens may be sampled in the actual order of HCV, HCV, HBV, HCV, HBV, HIV, and HIV, or may be sampled for each assay item. At this time, "completion of measurement for control materials" 509 is carried out during measurement of the patient specimens. When the "determination information of control material" 509 is satisfactory (OK), "continue of sampling of patient specimen" 511 is carried out. When the "determination information of control material" 509 indicates a fault (NG), the step of "stopping sampling of the corresponding specimen" 513 is carried out. As a more specific example, the group of control materials of HCV, HBV, and HIV is measured in the above-mentioned order, and a result indicating the satisfactory HCV group of control materials is obtained. When the determination information indicating the analysis result of the HBV group of control materials indicates an error and warning is displayed, sampling of the patient specimen of HCV is continued and sampling of the patient specimen of HBV is stopped. At this time, when the measurement of the group of control materials of HIV is not completed and the determination result is not obtained, sampling of the patient specimen in the assay item of HIV may be continued. More preferably, "a setting indicating that sampling of a patient specimen is temporarily stopped during another fault of control material" 606 can be input on the setting screen of the input unit. When the setting 606 is input, sampling of the patient specimen of HIV is temporarily stopped. After that, when the measurement for control materials of HIV is completed and the determination information is satisfactory, sampling of the patient specimen of HIV is resumed. On the contrary, when the determination information indicates fault, sampling of the patient specimen HIV is completely stopped. Thus, sampling is temporarily stopped based on the measurement result in another assay item, thereby avoiding unnecessary consumption of patient specimens and expensive reagents or consumables in genetic tests when the fault is not caused due to an assay reagent but is caused due to a common cause. Further, when the measurement result for control materials is satisfactory, the analysis of the patient specimen that should be analyzed even if a tester is not present can be advanced by automatically resuming the analysis.

Next, as illustrated in FIG. 6B, the setting screen includes "setting for measuring a patient specimen only in a normal item of control material after completion of measurement for control materials" 603 as an item for setting for waiting for the measurement result for control materials as a sampling timing for the patient specimen. When the user inputs the setting 603, after the "completion of measurement for control materials" 505 is carried out, "sampling of a patient specimen" 507 is automatically started when the result of control material shows the satisfactory determination (OK) based on the "determination information of control material" 506. When the measurement result for control materials indicates a fault (NG), "completely stop sampling of the corresponding specimen" 513 is carried out to avoid measurement of sampling of the patient specimen when the measurement result for control materials indicates a fault, thereby avoiding unnecessary consumption of patient specimens and expensive reagents or consumables.

As another operation process in the above-described device configuration, the user inputs "a setting indicating that a group of control materials is measured if necessary" 503 on the setting screen in association with the device operation process. The user installs the patient specimen group (in the order of HCV, HCV, HCV, HCV, HBV, HCV, HBV, HBV, HBV, HBV, HIV, HIV, HBV, HIV, and HIV) and the group of control materials corresponding to the patient specimen group in the specimen holding unit 102. An assay reagent is installed in the assay reagent installation unit 305. When the start button is pressed, the device that implements this embodiment first starts "sampling of a group of control materials" 520 corresponding to HCV which is located first in order when the specimens are arranged in the order of priority of measurement. Preferably, as illustrated in FIG. 6B, the setting screen includes a setting for "start measurement of a patient specimen after sampling of control material" 604. As a specific example, after completion of sampling of the group of control materials corresponding to HCV, sampling of the patient specimen of HCV is started without waiting for completion of measurement of the group of control materials. In the case where the measurement time for the assay item is long, the throughput is extremely lowered after waiting for the completion of measurement of the group of control materials, and thus a maximum throughput can be ensured by starting sampling of patient specimens without waiting for the completion of the measurement.

On the other hand, as illustrated in FIG. 6B, on the setting screen, the user can input a setting indicating waiting for a measurement result for control materials. For example, the setting screen includes the setting for "measurement of a patient specimen only in the normal item of control material after completion of measurement for control materials" 603. In this case, after "completion of measurement for control materials" 522, when the determination is satisfactory (OK) based on "determination information of control material" 523, "start sampling of a patient specimen" 524 is automatically carried out. On the other hand, when the determination is fault (NG), "stop sampling the patient specimen in the item corresponding to the group of control materials" 529 is carried out. Consequently, unnecessary consumption of patient specimens and expensive reagents or consumables when the measurement result for control materials indicates a fault can be suppressed.

As a specific example of the process described above, sampling of the group of control materials of HBV is carried out after sampling four patient specimens of HCV and immediately before sampling the patient specimen of HBV. After completion of sampling of all control materials, sampling of the patient specimen of HBV is started without waiting for completion of measurement of the group of control materials. The effect of promptly starting sampling is described above. Preferably, the setting screen includes an item for setting whether or not to wait for the measurement result for control materials as a patient specimen sampling timing. When a setting for waiting for the measurement result for control materials is input, the measurement for control materials is completed. When the determination is satisfactory based on the determination information, sampling of a patient specimen is automatically started. When the determination indicates fault, sampling of the patient specimen is stopped. Consequently, unnecessary consumption of patient specimens and expensive reagents when the measurement result for control materials indicates a fault can be suppressed.

Since the sampling of control material for the patient specimen of HCV which is disposed after one patient specimen HBV is sampled in the operation process described above is completed, the sampling is continued. When the setting for sampling after the measurement result only for the HCV item is obtained is input on the setting screen, sampling of the patient specimen of HCV is skipped. After that, sampling of the group of control materials of HIV is automatically started after four patient specimens of HBV are sampled and before the patient specimen of HIV is sampled. After completion of sampling of the group of control materials corresponding to HIV, sampling of the patient specimen of HIV is started without waiting for completion of measurement of the group of control materials. The effect of promptly starting sampling is described above. Preferably, the setting screen includes an item for setting whether or not to wait for the measurement result for control materials as a patient specimen sampling timing. When the setting for waiting for the measurement result for control materials is input, the measurement for control materials is completed. When the determination is satisfactory based on the determination information, sampling of a patient specimen is automatically started. Consequently, in the case of an assay item with a short measurement time, unnecessary consumption of expensive reagents when the measurement result for control materials indicates a fault can be suppressed without any adverse effect on the throughput.

Specific examples of the case where the priority order is the order of arrangement have been described above. However, when the priority order is the order of assay items, the setting screen includes a screen for setting the priority order of assay items, or means capable of determining the priority order using assay items, such as the installation number of assay reagents used as the priority order of assay items. At this time, sampling of the patient specimen corresponding to the control material after measurement for control materials with high priority may be carried out. The operation settings at this time are described above with regard to the order of priority.

Next, an operation process in which, for example, measurement result information about a patient specimen is automatically reported to an administer of a higher level via HOST communication will be described. Automatic reporting in this embodiment refers to automatic transmission of measurement result information to a computer located outside of the device via a network.

Figure 6C:
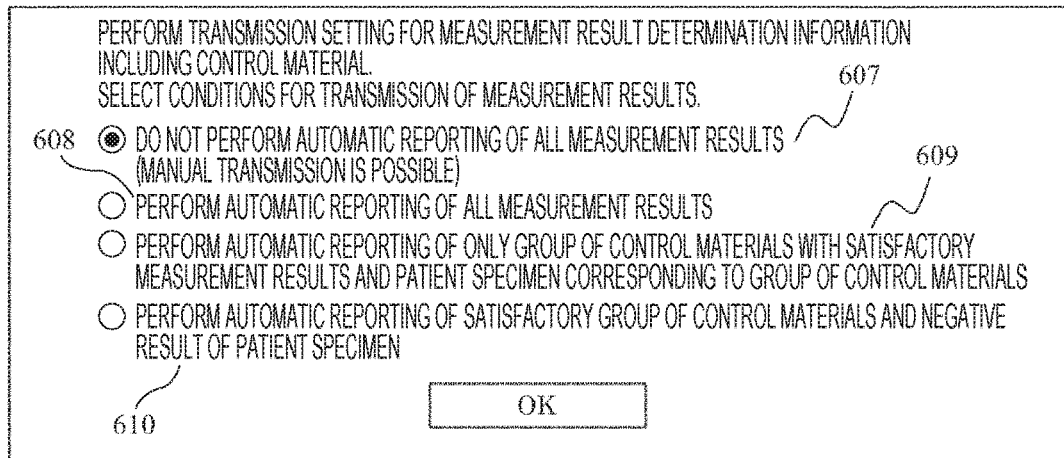
FIG. 6C is a diagram illustrating a specific example of the screen setting for control material.

On the setting screen as illustrated in FIG. 6C in association with the device operation process, the input unit of the device that implements this embodiment includes, as conditions for automatically reporting measurement results of patient specimens, "do not perform automatic reporting of all measurement results" 607, "perform automatic reporting of all measurement results" 608 including the results of the group of control materials, "automatic reporting of only the group of control materials with the satisfactory measurement result and the patient specimen corresponding to the group of control materials" 609, and "perform automatic reporting when the group of control materials is satisfactory and the result of the patient specimen is negative" 610. When each setting is input, the measurement result information is automatically reported according to the setting.

More specifically, when the setting item "do not perform automatic reporting of all measurement results" 607 is input, the device that implements the invention does not automatically transmit measurement result information even if any measurement results are obtained. At this time, a button for manual transmission may be placed on the screen of the device, and only the information selected by the user may be transmitted when the user presses the button. When the setting item "perform automatic reporting of all measurement results" 608 is input, the device that implements the invention automatically reports all pieces of measurement result information even if any measurement results are obtained. In the case where the setting item "perform automatic reporting of a group of control materials with a satisfactory measurement result and the patient specimen corresponding to the group of control materials" 609 is input, if a measurement fault is present in any of the groups of control materials other than the internal control material, the device that implements the invention does not perform automatic reporting of the measurement result of the patient specimen corresponding to the control material. When all measurement results are satisfactory in the groups of control materials other than the internal control material, the patient specimen with a satisfactory measurement result for the internal control material is automatically reported. As described above, the automatic reporting conditions can be set depending on the result of each control material, so that the automatic reporting can be performed in accordance with the policy of the test laboratory.

More specifically, in the case where the setting item "perform automatic reporting when the group of control materials is satisfactory and the result of the patient specimen is negative" 610 is input, if a measurement fault is present in any one of the groups of control materials other than the internal control material, automatic reporting of the measurement result of the patient specimen corresponding to the control material is not performed, and when all measurement results of the groups of control materials other than the internal control material are satisfactory and the measurement result of the internal control material shows a satisfactory positive result for the patient specimen, the measurement result is suspended and is not automatically reported. When the patient specimen shows a negative result, the negative result as well as the positive results which have been suspended is automatically reported. In the case of a test laboratory in which, when the internal control material is satisfactory, it can be ensured that the analytic process is satisfactory, but the possibility that contamination occurs due to, for example, contamination of the laboratory, is taken into consideration, a risk of amplification determination in all specific assay items cannot be excluded. Therefore, automatic reporting of the measurement result is performed after the possibility that all the negative determinations in the measurement results of the patient specimens are amplified is excluded, thereby enabling automatic reporting of the measurement results with a high reliability.

Further, in the operation for control material setting illustrated in FIG. 6A, when there is a laboratory that is intended to measure a control material so as to confirm the quality of the measurement result again after completion of measurement of a patient specimen, a preliminarily set (group of) control material automatically after completion of measurement can be automatically measured. For example, the setting item "perform automatic setting of a group of control materials set after completion of measurement of a patient specimen" 616 is provided. When the user inputs the setting, the device that implements the present invention can hold the set group of control materials in the specimen holding unit 102, and can automatically sample and measure the group of control materials after completion of measurement of the patient specimen.

Further, a flag may be added to the result information about each patient specimen by setting, for the measurement result information of each patient specimen, the state in which the test result is completely ensured by all measurement results for control materials as "determined", and by setting a state in which any one of the measurement results for control materials lacks as "pending". At this time, as illustrated in FIG. 6E, a setting item "perform automatic reporting of only the determined result" 614 and a setting item "perform automatic reporting of results including pending results" 615, the user can select these settings. The device that implements the present invention in which the setting "perform automatic reporting of only determined results" 614 is input transmits only the satisfactory patient specimen results indicated by the determination information about all the measurement results for control materials including the internal control material to a higher level. On the other hand, the device that implements the present invention in which the setting "perform automatic reporting of results including pending results" 615 is input transmits the results promptly to the higher level even if the result information of control material is insufficient at the time when the measurement result is obtained. At this time, if the transmitted result is "pending", the determination information obtained when the measurement result is "determined" is transmitted to the higher level again. With this configuration, measurement results can be automatically reported to the higher level promptly without waiting for all the results of control material in the device that continuously analyzes specimens.

Further, the operation process for automatically stopping sampling in the case where an amplification determination is continuously made due to, for example contamination of a laboratory, will be described. On the setting screen as illustrated in FIG. 6D in association with the device operation process by the input unit of the device, the device that implements the present invention includes, for example, a setting item "do not automatically stop sampling" 611 and a setting item "automatically stop sampling when a predetermined amplification determination is continuously determined" 612. The setting item 612 is configured to be able to perform stop setting for each item and input a numerical value indicating the number of continuous amplification determinations of the patient specimen. In the case where the numerical value "20" indicating the number of continuous amplification determinations is set on the setting screen, automatic sampling is stopped when 20 or more amplification determinations are continuously obtained during a period in which the device measures patient specimens.

By stopping the sampling, a measurement that causes a test fault due to occurrence of a risk, such as contamination of a laboratory, can be suppressed and unnecessary consumption of specimens and expensive reagents or consumables can be suppressed.

More preferably, the number of continuous amplification determinations can be set for each assay item, and sampling of patient specimens in the assay items with different numbers of continuous amplification determinations for each assay item is skipped. More preferably, the negative control material is constantly held in the device and when the number of continuous amplification determinations has reached a set value, the negative control material is automatically sampled and sampling of the patient specimen is temporarily stopped. When the measurement result for the negative control material is normal, sampling of the patient specimen is continued, and when the negative control material is abnormal, sampling of the patient specimen corresponding to the assay item is skipped. As described above, the negative control material is constantly held in the holding unit and the provision of the configuration of the holding unit and the dispensing unit in this embodiment makes it possible to convey a control material to be measured to a dispensing position at any timing, automatically measure the negative control material by dispensing the object, and interrupt sampling during measurement of the negative control material, so that the presence or absence of a risk of contamination of a laboratory is automatically determined and when there is no problem, the test can be automatically resumed even if a tester is not present.

Note that the present invention is not limited to the embodiments described above and includes various modified examples. For example, the above embodiments are described in detail to facilitate the explanation of the present invention, and thus are not limited to the invention including all the configurations described above. A part of the configuration of a certain embodiment can be replaced by the configuration of another embodiment. The configuration of a certain embodiment can be added to the configuration of another embodiment. For apart of the configuration of each embodiment, addition, deletion, or replacement of another configuration can be made.

A part or the whole of the configurations, functions, processing units, processing means, and the like described above may be implemented by hardware, for example, by designing the hardware using an integrated circuit. The configurations, functions, and the like described above may be implemented by software by interpreting and executing a program for causing a processor to implement each function. Information such as a program, a table, or a file for implementing each function can be stored in a recording device such as a memory, a hard disk, or an SSD (Solid State Drive).

Control lines and information lines necessary for explanation are herein illustrated, and all the control lines and information lines are not necessarily shown in products. In practice, almost all configurations may be connected to each other.

The invention claimed is:

1. An automated analyzer comprising:
  a dispensing unit;

a plurality of control materials, including positive and negative control materials:

a holder configured to hold the plurality of control materials, which are accessible as needed by the dispensing unit;

a processor configured to perform sampling of a patient specimen/control material;

an analyzer configured to perform an assay of the sampled patient specimen/control material;

a data analyzer configured to analyze a result of the assay;

a database that holds a plurality of operation processes for the plurality of control materials:

an input interface via which the operation processes are selected; and a control unit configured to control the dispensing unit, the holder, the processor, the analyzer, the data analyzer, the database, and the input interface, wherein a patient specimen sampling timing is preliminarily settable, as a setting item, where the patient specimen sampling timing is settable as a time before or after completion of measurement for control materials, and the control unit is configured to control operation processes for control material/patient specimen by:
1) starting the sampling by giving priority to an entirety of control materials corresponding to all assay items required for measurement;
2) automatically starting sampling of a patient specimen based on the patient specimen sampling timing that is preliminarily set after completion of sampling of the entirety of control materials; and
3) stopping, when an abnormality is present in a measurement result of at least any one control material in the plurality of control materials, sampling of a patient specimen corresponding to the control material in which the abnormality is found, and notifying a tester of the abnormality;

wherein the input interface is configured to automatically set a measurement for the negative control materials when a predetermined number of positive test results are continuously detected;

wherein an assay of the negative control material is automatically performed when a predetermined number of continuous positive test results are obtained for a setting for instructing a measurement for control materials in the setting item, and when the negative control material is determined to be abnormal, a user is informed of the abnormality; and wherein when no abnormality is present in a measurement for control materials result for a patient specimen temporarily stopped before completion of measurement for control materials, the temporarily stopped sampling of the patient specimen is automatically resumed.

2. The automated analyzer according to claim 1, wherein when an abnormality is present in a measurement result of the plurality of control materials in a certain assay item, the automated analyzer is configured to temporarily stop sampling of a patient specimen corresponding to the plurality of control materials before completion of measurement of another assay item.

3. The automated analyzer according to claim 1, wherein when a positive test result is obtained for a measurement result of a patient specimen measured in an M-th order, transmission of measurement result information is suspended, and when a measurement result of a patient specimen measured in an (M+I)-th order or later shows a negative determination and a result of internal control material shows a normal determination, the measurement results and the suspended measurement result information obtained in the M-th measurement are transmitted.

4. The automated analyzer according to claim 3, wherein the input interface for selecting operation processes includes a setting item for selecting whether or not a measurement for control materials is required after completion of measurement, and
a control material that is automatically set after completion of requested measurement is measured according to a setting for instructing a measurement for control materials in the setting item.

5. An automated analyzer comprising:
a dispensing unit;
a plurality of control materials, including positive and negative control materials:
a holder configured to hold the plurality of control materials accessible as needed by the dispensing unit;
a processor configured to perform sampling of a patient specimen and/or control material;
an analyzer configured to perform an assay of the sampled patient specimen and/or control material;
a data analyzer configured to analyze a result of the assay;
a database that holds a plurality of operation processes for the plurality of control materials:
an input interface via which the operation processes are selected; and
a control unit configured to control the dispensing unit, the holder, the processor, the analyzer, the data analyzer, the database, and the input interface, the automated analyzer being configured to operate control material, patient specimen and/or measurement result information according to a preliminarily set operation process, wherein
a patient specimen sampling timing is preliminarily settable, as a setting item, where the patient specimen sampling timing is settable as a time before or after completion of measurement for control materials, and the control unit is configured to control operation processes for control material/patient specimen by:
1) starting sampling by giving priority to an entirety of control materials corresponding to an assay item having an N-th highest priority and required for measurement and automatically starting sampling of a patient specimen corresponding to the plurality of control materials in accordance with the setting item after completion of sampling of the entirety of control materials;
2) automatically starting sampling of a patient specimen corresponding to an assay item having an (N+I)-th highest priority after completion of patient specimen sampling corresponding to 1), and automatically starting sampling of a patient specimen corresponding to the plurality of control materials based on the setting item after completion of sampling of all the plurality of control materials; and
3) stopping, when an abnormality is present in a measurement result of at least any one of control materials in the plurality of control materials, sampling of a patient specimen corresponding to the control material in which the abnormality is found, and notifying a tester of the abnormality;

wherein the input interface is configured to automatically set a measurement for the negative control material when a predetermined number of positive test results are continuously detected; and wherein an assay of the negative control material is automatically performed when a predetermined number of continuous positive test results are obtained for a setting for instructing a measurement for control materials in the setting item, and when the negative control material is determined to be abnormal, a user is informed of the abnormality; and wherein during an automatic analysis of the negative control material, an assay of a patient specimen is stopped, and when a result of the assay of the negative control material is normal, the measurement is ready to resume.

6. The automated analyzer according to claim 5, wherein the input interface for selecting an operation process is configured to input a numerical value as the number of continuous positive test results for each inspection item, and an automatic operation can be performed according to the setting.

* * * * *